(12) United States Patent
Haymann et al.

(10) Patent No.: US 6,979,496 B2
(45) Date of Patent: Dec. 27, 2005

(54) MILL BLANK LIBRARY AND COMPUTER-IMPLEMENTED METHOD FOR EFFICIENT SELECTION OF BLANKS TO SATISFY GIVEN CRITERIA

(75) Inventors: Basil A. Haymann, Dallas, TX (US); Mark S. Quadling, Plano, TX (US); Henley S. Quadling, Addison, TX (US); Howard Frysh, Dallas, TX (US); Jorey A. Chernett, Plano, TX (US)

(73) Assignee: D4D Technologies, LP, Richardson, TX (US)

( * ) Notice: Subject to any disclaimer, the term of this patent is extended or adjusted under 35 U.S.C. 154(b) by 0 days.

(21) Appl. No.: 10/887,569

(22) Filed: Jul. 9, 2004

(65) Prior Publication Data

US 2005/0008887 A1    Jan. 13, 2005

Related U.S. Application Data

(60) Provisional application No. 60/485,935, filed on Jul. 9, 2003.

(51) Int. Cl.$^7$ .................. A61C 13/00; A61C 13/08; A61C 13/113
(52) U.S. Cl. .................. 428/542.8; 433/201.1; 433/223; 433/229
(58) Field of Search .................. 433/167, 171, 433/201.1, 206, 202.1, 208, 212.1, 213, 215, 433/223, 218, 226, 229; 241/24.1, 24.12, 241/24.25; 428/542.8

(56) References Cited

U.S. PATENT DOCUMENTS

| | | | |
|---|---|---|---|
| 4,615,678 A | * | 10/1986 | Moermann et al. ...... 433/201.1 |
| 5,273,428 A | | 12/1993 | Fischer |
| 6,345,984 B2 | * | 2/2002 | Karmaker et al. .......... 433/173 |
| 2002/0076530 A1 | * | 6/2002 | MacDougald et al. ...... 428/195 |
| 2003/0031984 A1 | * | 2/2003 | Rusin et al. ................ 433/215 |
| 2004/0185422 A1 | | 9/2004 | Orth et al. |

OTHER PUBLICATIONS

VITA CEREC(R) Produkte/Products, Nov. 2000 (Edition), Germany.

* cited by examiner

*Primary Examiner*—Michael E. Lavilla
(74) *Attorney, Agent, or Firm*—David H. Judson

(57) ABSTRACT

The present invention relates generally to mill blank constructions to facilitate the manufacture of dental restorations. A given mill blank is formed in a shape (i.e. with a given geometry) that has been predetermined to reduce material waste when the mill blank is machined into the final part. A set of two or more blanks each having such characteristics comprise a smart blank "library." In one embodiment, a smart blank library includes a sufficient number of unique blanks such that, when the geometry of the designed restoration is known, the smart blank with a highest yield can be selected for use in milling the restoration. The "yield" of a given smart blank represents the amount of material of the smart blank that is actually used in the final restoration. Automated processes for smart blank inventory management and smart blank selection are also described.

15 Claims, 10 Drawing Sheets

200

MILL BLANK LIBRARY AND COMPUTER-IMPLEMENTED METHOD FOR EFFICIENT SELECTION OF BLANKS TO SATISFY GIVEN CRITERIA

This application is based on and claims priority from Provisional Patent Application Ser. No. 60/485,935, filed Jul. 9, 2003.

BACKGROUND OF THE INVENTION

1. Technical Field

This invention generally relates to a system for preparing dental prostheses. In particular, the invention relates a smart mill blank library and preparing dental prostheses for use as crowns, onlays, inlays, veneers, bridges, and other restorations from a mill blank selected from a mill blank library.

2. Related Art

The art of fabricating custom-fit prosthetics in the dental field is well-known. Prosthetics are replacements for tooth or bone structure. They include restorations, replacements, inlays, onlays, veneers, full and partial crowns, bridges, implants, posts, and the like. Typically, a dentist prepares a tooth for the restoration by removing existing anatomy, which is then lost. The resultant preparation may be digitized or a dental impression is taken, for the purpose of constructing a restoration. The restoration may be constructed through a variety of techniques including manually constructing the restoration, using automated techniques based on computer algorithms, or a combination of manual and automated techniques. In one known technique, the prosthetic is fabricated using a computer-assisted (CAD/CAM) system, such as a computer-aided milling machine. One such machine is the CEREC 3D system from Sirona Dental Systems. Computer-aided machines of this type work by shaping the prosthetic from mill blanks. A mill blank is a solid block of material from which the prosthetic is shaped by a shaping apparatus whose movements are controlled by the computer. Under computer control, the size, shape, and arrangement of the restoration may be subject to various physical parameters, including neighboring contacts, opposing contacts, emergence angle, and color and quality of the restoration to match the neighboring teeth.

A common restoration includes a porcelain-fused-to-metal (PFM) crown. The crown typically comprises a cap of porcelain material overlayed on a thin metal coping. The metal coping forms an interface between the preparation and the porcelain material. Common restorations typically include a coping formed from precious or semi-precious metals, including gold or a gold alloy. The material may be selected based on the color and various other properties to optimize a long-lasting natural looking restoration.

The copings or full metal crowns typically are formed from a lost wax casting process. The process may include placing several wax copings on a wax tree, which is connected to a wax base. The structure is placed in a cylinder with investing material, and the wax is melted out after the investing material has set. A molten metal, typically a gold alloy, is then poured into the remaining structure, and the entire cylinder is placed into a centrifuge to distribute the molten material to a uniform distribution. Preferably, the alloy base and the tree are recovered for use in a future casting process. The continued re-melting of the gold alloy along with other contaminants, however, introduces oxidation and other tarnishing agents into the gold alloy.

Other methods for forming the coping may be used, including milling or machining with some kind of block or blank, but these techniques may waste much of the metal material. The ratio of the volume of the final metal coping to the volume of a typical enclosing mill blank (a symmetric block or cylinder) is often very small such that much of the material may be wasted. As noted above, a common milling process includes forming the coping from a mill blank using a computer-assisted milling machine. The blank includes a sufficiently large rigid attachment so that it may be held solidly while the machining process is underway. A rectangular or cylindrical blank is commonly used, and the vast majority of material is removed via the machining process. U.S. Pat. No. 4,615,678 to Moermann et al. discloses a conventional mill blank of this type made of ceramic silica material. There are, of course, numerous other types of mill blanks available commercially.

The cost of recovering the wasted material often exceeds the cost of the material sought to be recovered. The object may be milled using a wet milling process, which typically results in the discarded material (including fine particles) being mixed with water or other cutting fluids. This is not a significant concern when the restoration is being formed using inexpensive materials; however, when utilizing expensive materials, such as gold, the issue of dealing with the recovery of the machined material may make the process prohibitively expensive. Indeed, the cost of the discarded materials in the case of precious or semi-precious materials is the single most important reason that prior art techniques have proven to be undesirable or cost prohibitive. Additional concerns are the time required to cut through the discarded material, as well as the additional wear and tear on the tools.

There have been a few incidental suggestions in the art to address this problem. Thus, for example, U.S. Pat. No. 4,615,678 teaches that the body portion of a mill blank can be formed in a way to minimize wear on and run time of the milling machine by being shaped initially to more closely resemble the final implant. An illustrative example is a blank for use in forming a two lobed inlay that includes a transverse groove in one side thereof. U.S. Published Patent Application 2003/0031984 to Rusin et al. illustrates a similar blank construction, and it further notes that blanks can come in a variety of shapes and sizes.

While these suggestions are useful, there remains a need in the art to provide improved mill blank configurations and assemblages that facilitate prosthetic milling operations in a manner to reduce material waste, reduce machining time, and to increase value.

BRIEF SUMMARY OF THE INVENTION

It is an object of the present invention to provide improved mill blank constructions to facilitate the manufacture of dental restorations. In general, this object is achieved by providing a given mill blank in a shape (i.e. with a given geometry) that has been predetermined to reduce material waste when the mill blank is machined into the final part. A mill blank that has been intelligently pre-configured into a form that more closely resembles the final dental part is sometimes referred to as a "smart" blank.

It is a further object of the invention to provide such mill blanks in a collection or "assemblage." A set of two or more smart blanks each having such characteristics is also sometimes referred to as a smart blank "library." In a preferred embodiment, it is desirable to provide a smart blank library that includes a sufficient number of unique blanks such that, when the geometry of the designed restoration is known, the smart blank with a highest yield can be selected for use in milling the restoration. The "yield" of a given smart blank represents the amount of material of the smart blank that is actually used in the final restoration, with the higher the yield value meaning the closer the "fit" of the smart blank to the designed restoration. In a particular embodiment, a smart blank library is maintained with a given number of unique blanks so as to balance an average yield per smart blank with a goal of satisfying an inventory requirement for the library (e.g., the smallest possible library size necessary to meet anticipated production requirements over a given time period). In this embodiment, it is desirable to have a sufficient number of unique smart blanks in the library such that the smart blank with a highest average yield can be selected and is available for use while ensuring that the number of blanks remains within a given inventory production factor.

According to a more specific embodiment, an assemblage of blanks comprises at least first and second smart blanks, with each smart blank adaptable for producing a formed part that can be used for replacement or restoration of one or more teeth by removing as little material from the blank as possible (i.e., an optimize yield). The first blank has a first geometry, and the second blank has a second geometry that differs from the first geometry other than by mere scaling. The first blank is configured to resemble a first given restoration, and the second blank is configured to resemble a second given restoration. Each of the blanks further includes a holder (a sprue) for mounting the blank in a shaping apparatus. The blank comprises a precious or semi-precious material, a ceramic silica material, or other material suitable for the substructure or final restoration.

It is another more general object of the invention to provide a smart mill blank library that comprises multiple smart mill blanks having a variety of predetermined shapes, sizes, and arrangements. Preferably, a given smart mill blank in the library is pre-formed to a target size, shape and arrangement so that the library as a whole is useful across for a particular set of applications. Thus, depending on the type and nature of the restoration, a particular smart mill blank is selected from the library and used in the milling operation. As a result, the amount of material needed to be removed from the mill blank is reduced greatly. This is especially desirable and cost-effective when precious or semi-precious materials (such as gold) are being used in the restoration. Indeed, use of a smart blank pre-formed from gold significantly reduces the amount of gold to be recovered, in many cases reducing it to less than that in a common lost wax casting process. In addition, the amount of time to machine the restoration is reduced due to a relatively small amount of material that needs to be removed from the smart mill blank. The use of such blanks provides further process advantages including, without limitation, reducing spoiling effects such as gold alloy tarnishing, eliminating trace metal oxidation, and the like.

Another more general object of the present invention is to provide a smart blank library that achieves maximum yield, so as to minimize material waste.

According to a specific feature of the present invention, the smart blank library comprises a set of copings or full contour crowns. A coping is the substructure of a crown. The general shape of a coping has an upper surface and a lower surface. The upper surface is generally a convex surface and the lower surface is generally a concave surface. The lower surface is configured to be able to be affixed to a dental preparation and to form a tight seal at a margin having a small but definite gap for cement. The general shape of the lower surface may mirror or correspond to the shape of a typical preparation. The general shape of the upper surface of the coping may correspond to an occlusal surface of a particular dental item. A selection of a smart mill blank from the library provides a more effective way to prepare a dental prosthesis and dental item to maintain optimal porcelain or other surface material on top of the metal coping.

In a common restoration, such as a porcelain-on-metal crown, it is desirable for longevity of the restoration to provide a substantially constant thickness of the porcelain material. Maintaining the constant thickness may reduce a risk of fracturing the material. Accordingly, in one embodiment, the smart mill blanks in the library may have a generally concavo-convex shape, with the top surface having a shape that allows the porcelain-sculpted anatomy to exhibit a near constant thickness Other methods, features and advantages of the invention will be, or will become, apparent to one with skill in the art upon examination of the following figures and detailed description. It is intended that all such additional methods, features and advantages be included within this description, be within the scope of the invention, and be protected by the following claims.

BRIEF DESCRIPTION OF THE DRAWINGS

The invention may be better understood with reference to the following drawings and its accompanying description. Unless otherwise stated, the components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

For illustrative purposes, the following terms may be afforded the following meanings in the context of the present invention:

A "blank" is a part adapted for use in custom fabrication of a dental restoration. Typically, a blank comprises a body for being shaped by material removal, and a holder (a "sprue") for mounting the blank in a shaping apparatus such as a CAD/CAM (or other) milling machine, device or system.

A "smart blank" is a blank that has been pre-configured into a form that, as compared to a conventional blank, much more closely resembles a restoration being designed.

A "yield" of a smart blank is the amount of material of the body part that ends up being useful for the restoration during the milling of the blank. According to the present invention, it is desirable to maintain a library of smart blanks such that, in use, an optimized yield per blank (and, thus, an optimized yield across the library as whole) is obtained.

Figure 1:
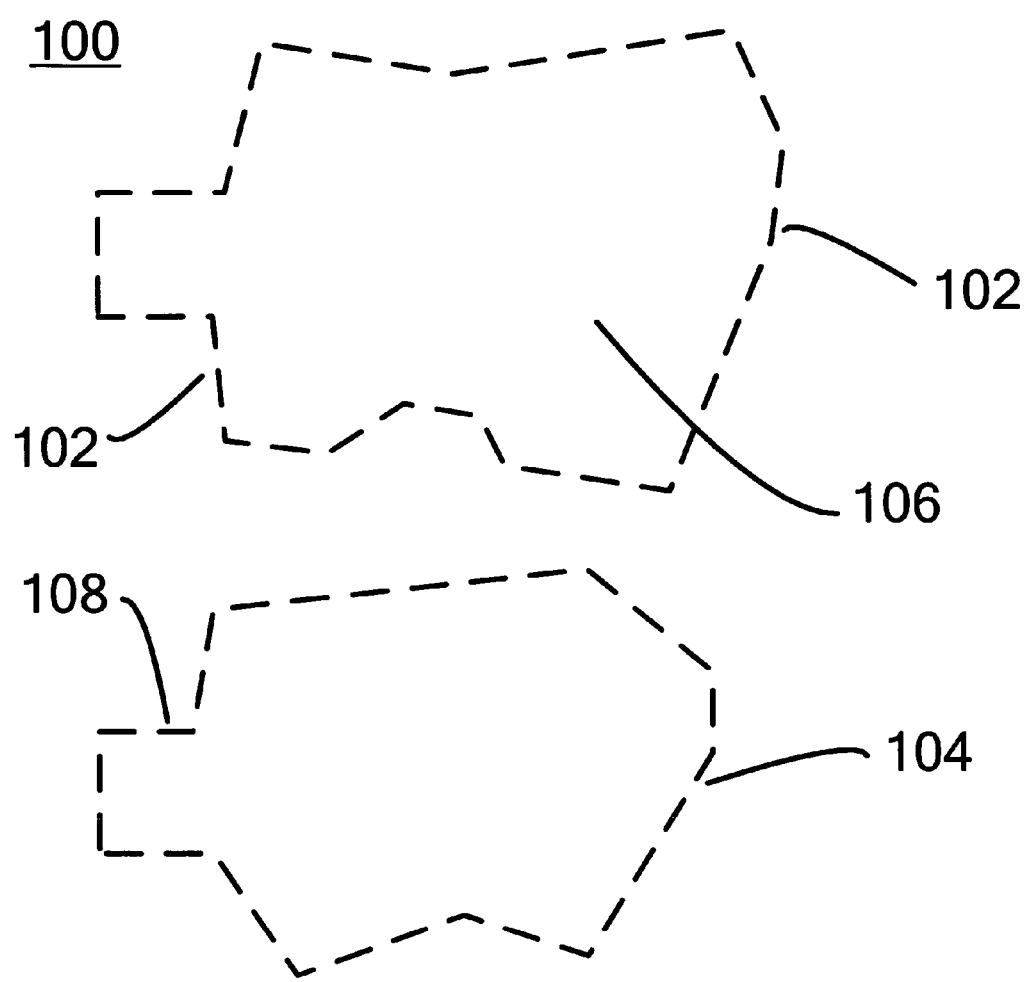
FIG. 1 illustrates a smart blank library according to an embodiment of the present invention.

A "library" (or "collection," or "assemblage") of smart blanks is a set of two or more smart blanks, with each blank adaptable for producing a formed part that can be used for replacement or restoration of one or more teeth, preferably by removing as little material from the blank as possible (i.e., to optimize yield per blank). Preferably, at least a first blank has a first geometry, and the second blank has a second geometry that differs from the first geometry by other than scaling. FIG. 1 illustrates a library 100 comprised of two blanks 102 and 104 that meet this criteria.

A "restoration" refers generically to a crown, coping, bridge, onlay, inlay, framework, or other dental item.

An "average yield per blank" is an average yield per blank, calculated as a weight of a finished restoration divided by a weight of an initial smart blank. Thus, e.g., if a milled coping weighs 1.5 penny weights and the smart blank (pulled from the library) weighs 3.0 penny weights), the average yield for this blank is 50%.

A "size" of the smart blank library refers to the number of unique smart blanks in the library.

A "production period" is an average number of restorations produced within a given dental laboratory or office over a given period (e.g., daily, weekly, monthly, or the like).

An "inventory over production factor" is the surplus, or amount of inventory that exceeds an average production for a given production period. Thus, assume the production period is daily. If a laboratory fabricates 40 restorations per day (200 per week) and 80 smart blanks per day (400 per week) are needed to fulfill production requirements, the inventory over production factor is 100%. A laboratory should have sufficient smart blanks to satisfy its production requirements for some specified period of time.

An "intrinsic cost of the average restoration" is the cost of the raw material used to create the finished restoration such as a coping.

A "distribution by tooth number" is a weighted distribution based upon laboratory productivity by tooth type (e.g., 27% $3^{rd}$ molar, 22%, $2^{nd}$ molar, 11%, $1^{st}$ molar, 14%, $2^{nd}$ bicuspid, 12%, $1^{st}$ bicuspid, and the like).

An "average scrap per smart blank" is one minus the average yield per smart blank.

A "scrap factor" is 100% divided by the average yield per smart blank. Thus, for example, if the average yield per smart blank is 50%, the scrap factor is 2.0).

A "cost per restoration" is the scrap factor times the intrinsic cost of the average restoration.

As noted above, FIG. 1 illustrates a smart blank library 100 that comprises at least a first smart blank 102, and a second smart blank 104. Each blank comprises a body 106 for being shaped by material removal, and a holder 108 for mounting the blank in a shaping apparatus. Preferably, the body 106 has a given geometry that will closely resemble a given restoration under design. Although not meant to be taken by way of limitation, preferably the body of a given smart blank has, at most, one symmetric plane. In this illustrative embodiment, the given geometry of the body of the first smart blank 102 differs from the given geometry of the body of the second smart blank 104 by other than scaling. The body may be formed of any suitable blank material including, without limitation, a precious metal or metal alloy, a semi-precious metal or metal alloy, a ceramic or other inorganic non-metallic material, or the like. The body is adapted to be formed or milled into any type of restoration (or other dental prosthetic) by hand or by a milling machine, such as a machine that uses a CAD/CAM system. Any convenient cutting technique can be used for this purpose.

More generally, a smart mill blank library comprises a plurality of smart mill blanks. The smart mill library includes a set of smart blanks having a pre-formed size shape and arrangement that approximates dental crown of various known tooth types and common dental preparations. The library may also include a set of smart mill blanks having a size, shape and arrangement that approximates copings for various types of teeth and common preparations.

Figure 2:
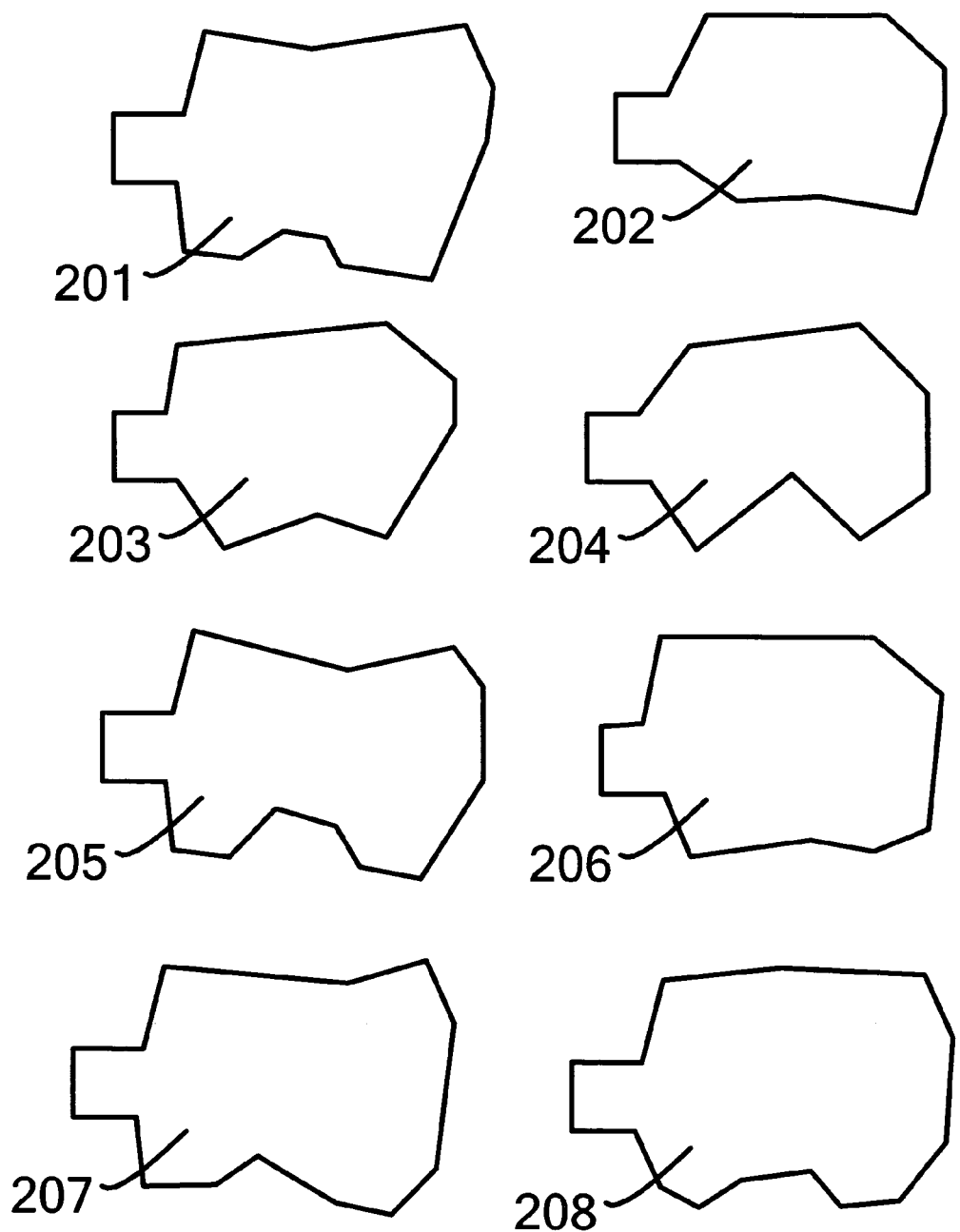
FIG. 2 illustrates another embodiment of the invention where the smart blank library has been sized to satisfy a given yield, productivity, cost or other factor.

FIG. 2 illustrates a smart library 200 as it is maintained in a given dental laboratory or office. It is assumed that this library has been drawn from a larger, global set of available smart blanks (a set that could be quite large in size theoretically given the variations in smart blank shapes). It is further assumed that the given dental laboratory or office only desires to maintain an inventory of smart blanks for which it expects to have demand and/or that satisfy some other inventory requirements. To this end, it is a further feature of the present invention to provide or maintain a smart blank library 200 of "n" smart blanks (as illustrated in the figure by a library of eight (8) smart blanks 201–208), where the library 200 has a smallest possible "size" (not necessarily of size 8, as illustrated) to satisfy a given criteria. One such criterion simply is the average yield per smart blank, as defined above. According to this example, the smart blank library 200 is sized with a set of unique blanks so that, when the geometry of the designed restoration is calculated or known (the particular technique by which this is done is not part of the present invention), an operator is provided with an indication of which smart blank to use, namely, the smart blank that offers the highest yield. In this example, this is the blank that is "closest" to the designed restoration, i.e., the blank with the least amount of material to be removed to satisfy the given design under construction.

Thus, in one embodiment, the smart blank library is stocked by selecting an assemblage of the blanks that satisfy a given criterion, where the given criterion is a maximum average yield per blank, and the smart blanks are then used to manufacture dental restorations. As an alternative, the given criterion is that a weighted average of the blank yields in the assemblage is maximized. Still another alternative criterion is that a weighted average of the blank yields in the assemblage is maximized. Another alternative criterion balances an average yield per blank with a given productivity factor. A further variant would be to use a criterion that balances an average yield per blank with a given cost factor.

Yet another given criterion balances among any of a set of yield, productivity, cost and/or tooth distribution factors, as more particularly described in the following paragraph by way of some specific examples.

One possibility to determine the library size is to use a given criterion that the average yield per smart blank be greater than a given selectable value for a given number of restorations for a given tooth (or tooth group), e.g., select a blank that results in at least a 70% yield for 80% of the restorations for a given tooth. The distribution by tooth number can be used to provide the data for this selection. Another way to maintain an appropriate library size is to enforce a highest average yield per blank while maintaining the inventory production factor within a given acceptable range. The inventory production factor may take into consideration the distribution by tooth number data as well. Still another criterion for sizing the library is to maintain smart blanks that exhibit a given yield within a given difference factor (e.g., a standard deviation, or multiple thereof) from a mean of a normal distribution of a tooth population. Another sizing criterion is to maintain sufficient smart blanks to facilitate trading off an average yield per smart blank and an intrinsic cost of the average restoration, thereby providing the operator with a blank that has a reasonably good yield but also considers the actual cost of the material being used.

The above are merely illustrative ways of maintaining a smart blank library in a cost-effective, demand-driven manner. Preferably, the sizing of the library (e.g., the selection of which blanks that the library will include) is done as an automated (computer-assisted) process, although this is not a requirement taking into consideration one or more of the above-described process variables. Generalizing, according to a feature of the invention, there are many possible criteria that may be used to determine the number (and possibly the types) of smart blanks to maintain in a given assemblage. In a preferred embodiment, the goal of optimizing yield typically is an important factor.

Figure 4:
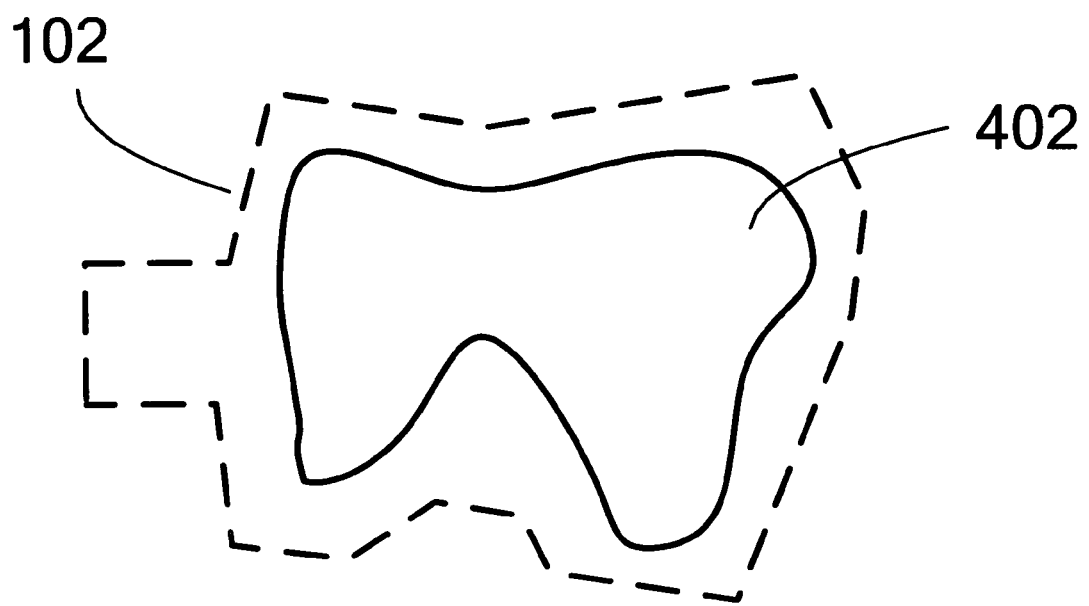
FIG. 4 illustrates how a first restoration is tested against a set of smart blanks in a given library to determine whether the restoration is containable therein.
Figure 4:
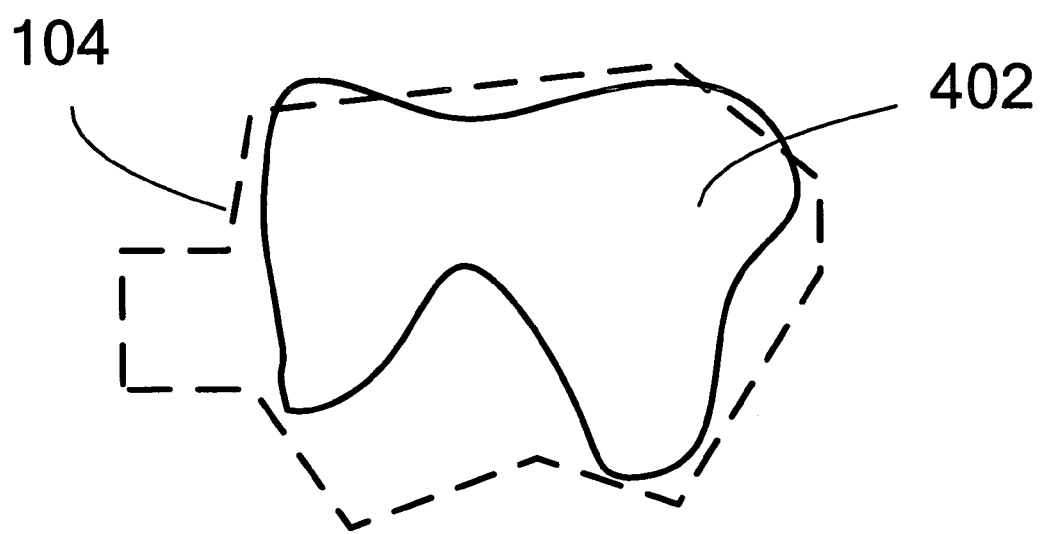
Figure 5:
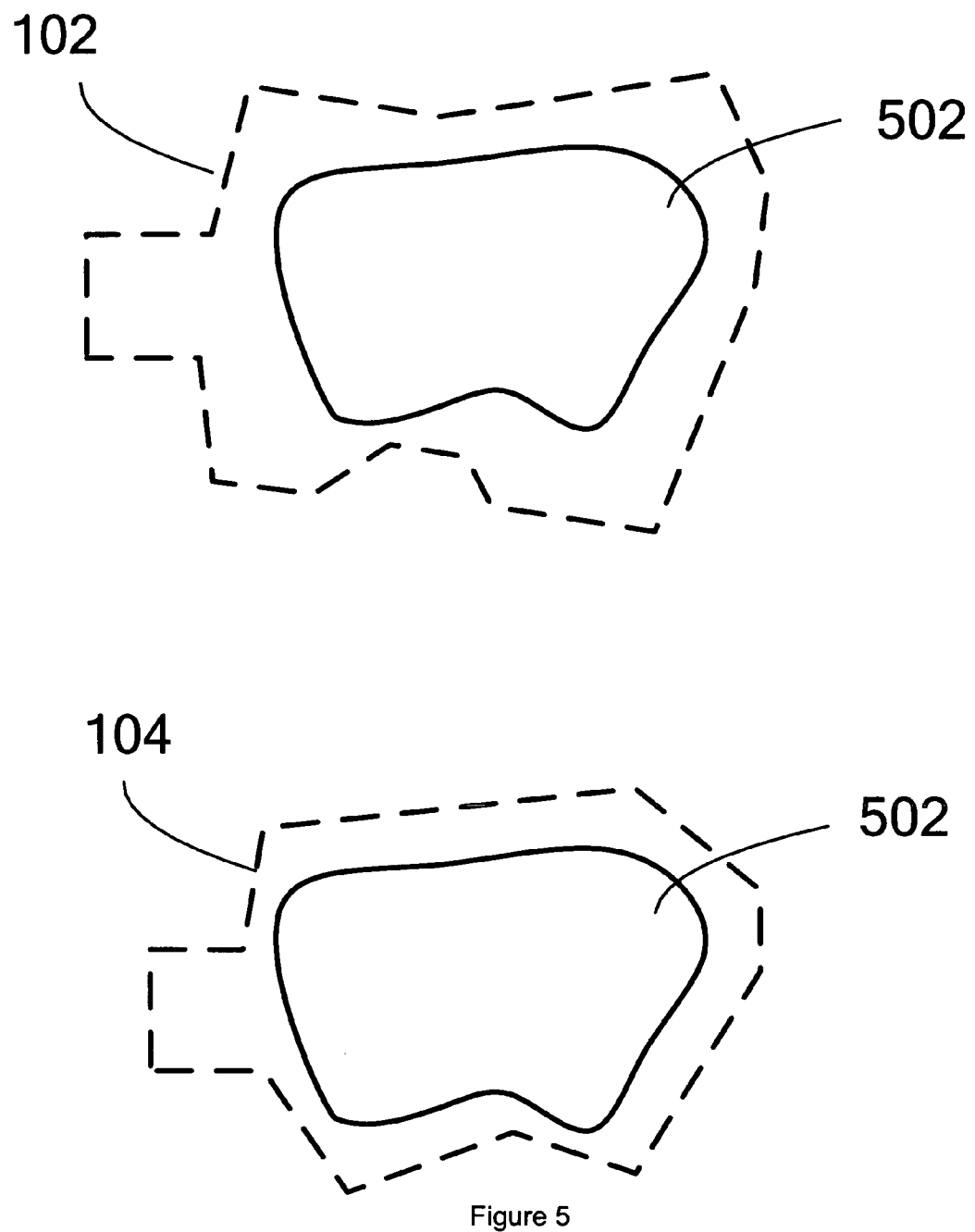
FIG. 5 illustrates how a second restoration is tested against the set of smart blanks in the given library of FIG. 4 to determine whether the restoration in containable therein.

It is now assumed that a smart blank library is being maintained (preferably according to one or more of the inventory techniques described above), and that a restoration is ready to be designed. The following description provides further details of a representative algorithm for selecting a smart blank in the library that is "closest" to the restoration being designed R. Without loss of generality, it is assumed that the restoration R is described in 3D by a closed polygon mesh or, more generally, by any other closed parameterized surface, such as Non-Uniform Rationale B-Spline surface (NURB). FIGS. 4 and 5 illustrate two such restorations 402 and 502. Of course, these shapes are merely exemplary. Continuing with the algorithm, it is assumed that each available blank $B_i$ in the library also is defined by a closed parameterized surface representation, where the size of the library is m. According to a preferred embodiment, a subset $\{B_1, B_2, \ldots B_n\}$ of n blanks is then selected, where each of the elements in the subset satisfies the following condition: $R \subseteq B_i$, for i=1, ... n. It should be noted that this condition is met only if there exists a relative transformation between R and B such that no point on R is visible from any vantage point outside of B. Stated another way, a blank that satisfies this condition is said to "contain" the restoration. Then, the blank of the subset with the smallest volume is selected as the blank from which the restoration R will be milled or machined. In particular, because each of the blanks of the subset contains the restoration, the one with the smallest volume will necessarily produce the highest yield. The above-described example is preferred, but variants are within the scope of the invention. Thus, instead of selecting the blank of the subset with the smallest volume (and thus the highest yield), an alternative would be to choose the blank with the second highest yield (for example, because inventory of the first blank may be too low, because the first blank is made from a material that is more costly than the material of the blank with a next highest yield, and so forth). As another alternative, instead of selecting the blank of the subset with the highest yield, a blank that has an acceptable yield may be chosen.

The above are merely representative examples. Any particular selection criteria (e.g., based on yield, productivity, cost, tooth distribution, or combinations of such variables) may be used to facilitate the smart blank selection process once the subset $\{B_1, B_2, \ldots B_n\}$ satisfying the containment condition has been determined.

Figure 3:
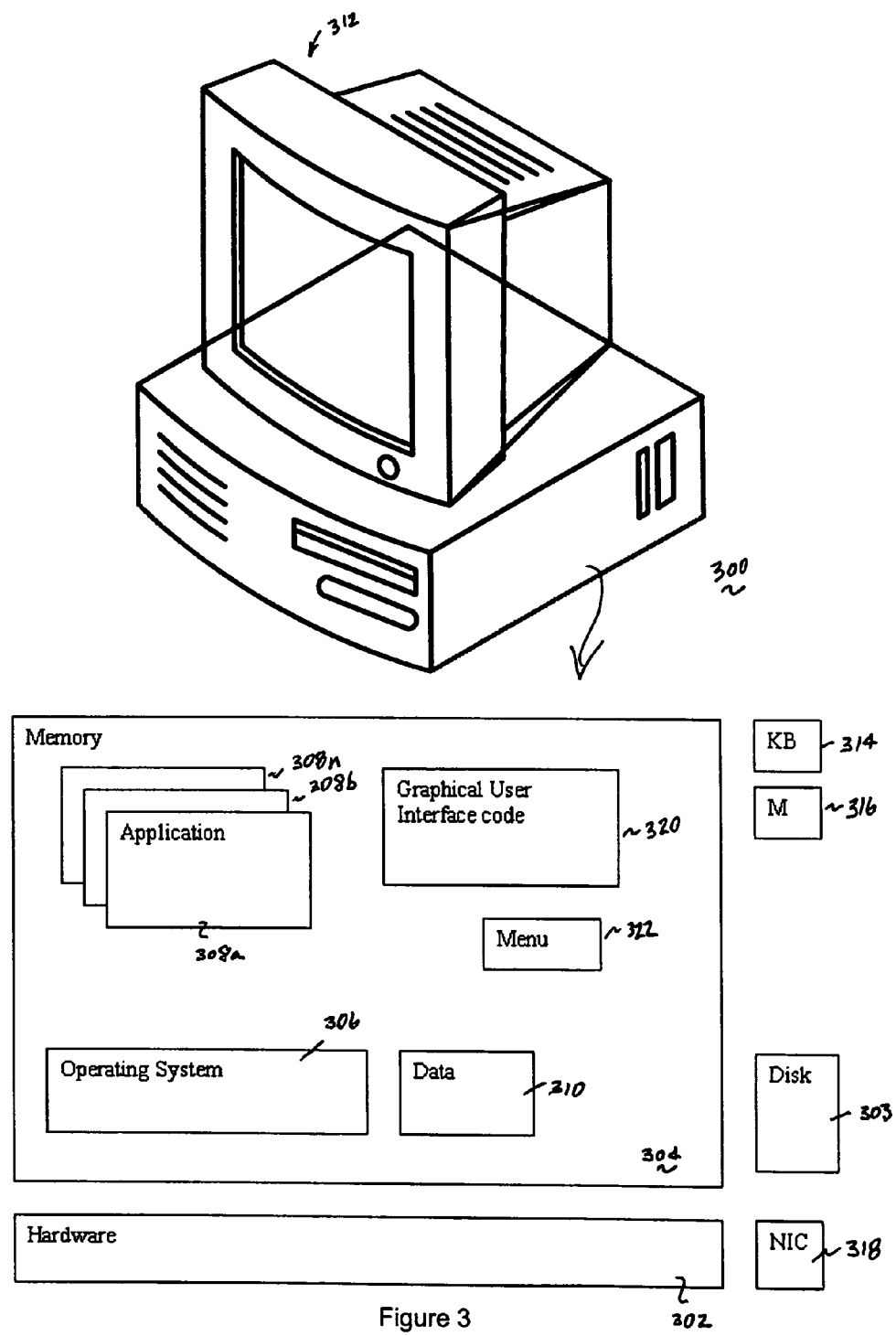
FIG. 3 illustrates a computer system that may be used to facilitate selection of a smart blank from the library of FIG. 2.

A computer or computer system as illustrated in FIG. 3 preferably is used to facilitate the above-described algorithm and selection process. An illustrative computer 300 comprises Intel-commodity hardware 302, suitable storage 303 and memory 304 for storing an operating system 306 (such as Linux, W2K, or the like), software applications 308a–n and data 310, conventional input and output devices (a display 312, a keyboard 314, a mouse 316, and the like), devices 318 to provide network connectivity, and the like. Using a conventional graphical user interface 320, an operator can select from a menu 322 given criterion by which the smart blank selection is to be effected, or create a custom criterion using one or more of the above-described variables (or other factors). In use, it is assumed that a given geometry of the designed restoration is made available to the computer system. The system has knowledge of the unique geometries of each of the smart blanks then available from the library. Using a given criterion (which the operator can select or that may be a default), the system then selects the smart blank from the available blanks that satisfies the given criterion, or that satisfies the given criterion within a given acceptance factor. As noted above, the present invention enables the operator to select the smart blank from the subset based on the factors it deems appropriate and suitable for its particular purposes.

Figure 6:
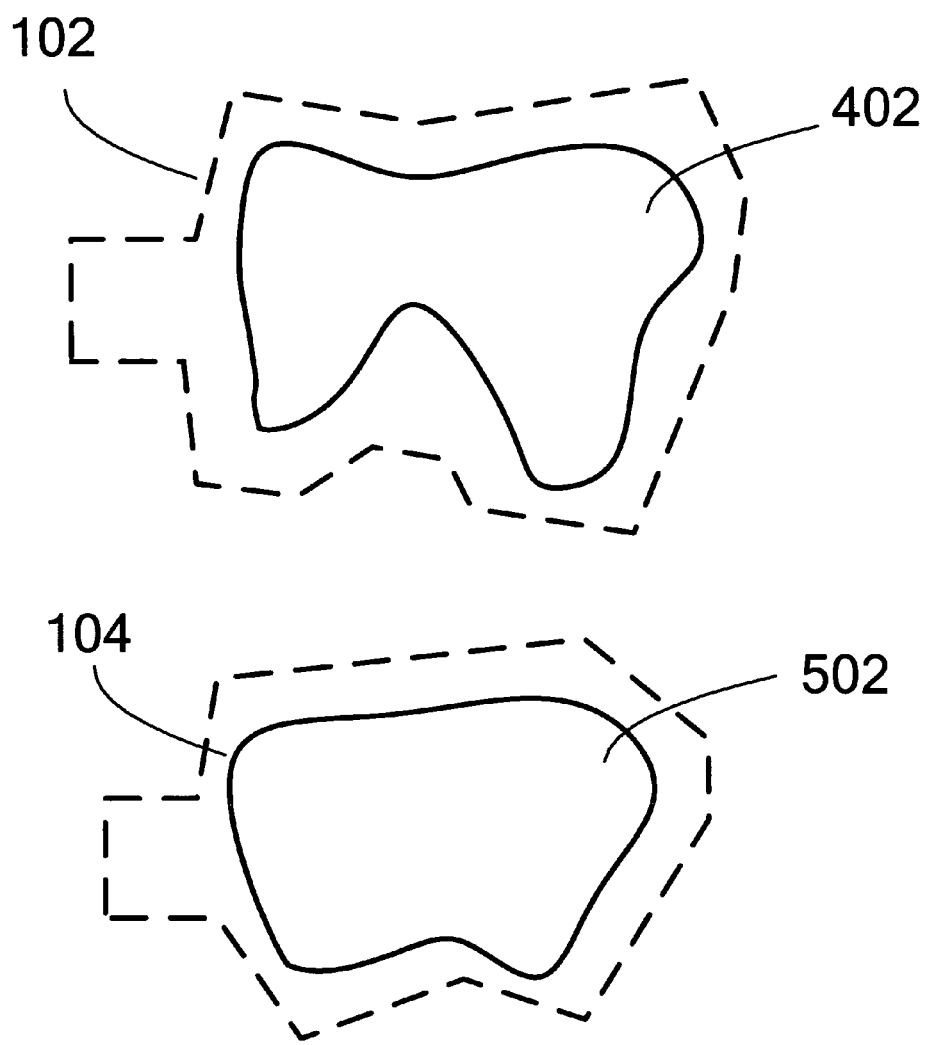
FIG. 6 illustrates the smart blanks selected for use in the manufacture of the first and second restorations.

As described above, the computer-implemented smart blank selection process first determines the subset $\{B_1, B_2, \ldots B_n\}$ of smart blanks that satisfy the containment condition. The subset determination for two different restorations given a smart library of two blanks 102 and 104 is illustrated in FIGS. 4–6. As seen in FIG. 4, the restoration 402 is containable within smart blank 102 but not within smart blank 104. Thus, for this particular restoration, only smart blank 102 would be a candidate for the final selection, i.e., only smart blank 102 is in the subset. In FIG. 5, however, the restoration 502 is containable within both smart blank 102 and smart blank 104; as a consequence, both blanks are candidates for the final selection, i.e., both are in the subset. In the preferred embodiment as has been described above, the smart blank of the subset with the lowest volume (thus, the highest yield) is then selected for use in milling the restoration. With respect to restoration 402, this condition does not matter (at least in this example), as blank 102 is the only blank in the subset. With respect to restoration 502, however, there are two choices. Accordingly, as seen in FIG. 6, smart blank 102 is used for the manufacture of restoration 402 while smart blank 104 (the one with the smallest volume) is used for the manufacture of restoration 502.

The following describes one computer-implemented technique for making a smart blank assemblage, although any particular technique (such as casting or forging) may be used. In general, a shape for the sets of smart blanks may be selected according to a particular application. Thus, for example, for each set, multiple (one hundred or more) cases are evaluated, where a digital impression is made of each preparation, for each type of preparation and for each tooth number in the American standard tooth numbering scheme. For each such preparation, an ideal crown or coping designed for that preparation is desired to be pre-formed as a smart blank, as described above. A percentage completed factor C is chosen. A standard mill blank (typically a block or cylinder) is then selected. The volume of material V to be removed from the standard mill block is then determined based on the dimensions of the mill block and the model of the final crown or coping to be milled. A target material removal volume U is calculated by U=CV/100. By way of example, V may be 100 mm$^3$ and C may be 60%, then U= 60 mm$^3$. The yield for the particular smart blank is then equal to 100%–C.

Figure 7:
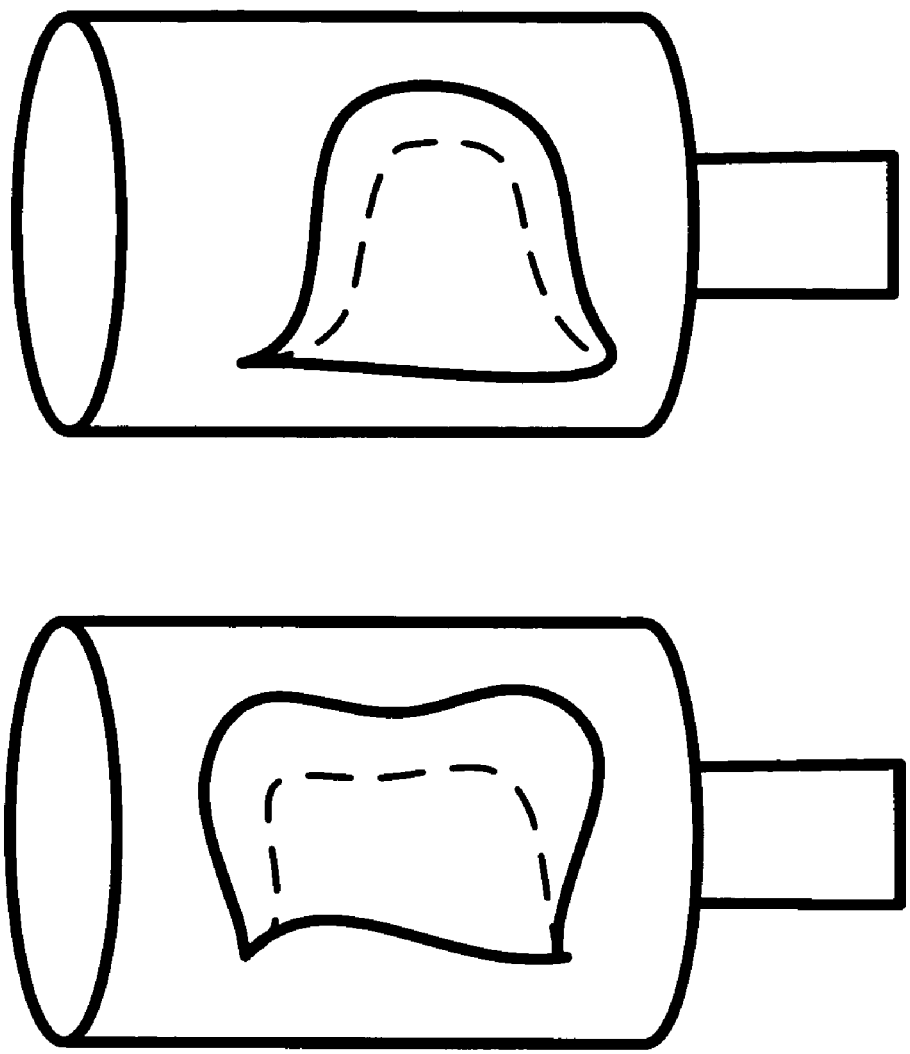
FIG. 7 illustrates conventional mill blanks each having a large amount of material that is discarded when the respective blank is shaped in a prior art milling process.
Figure 8:
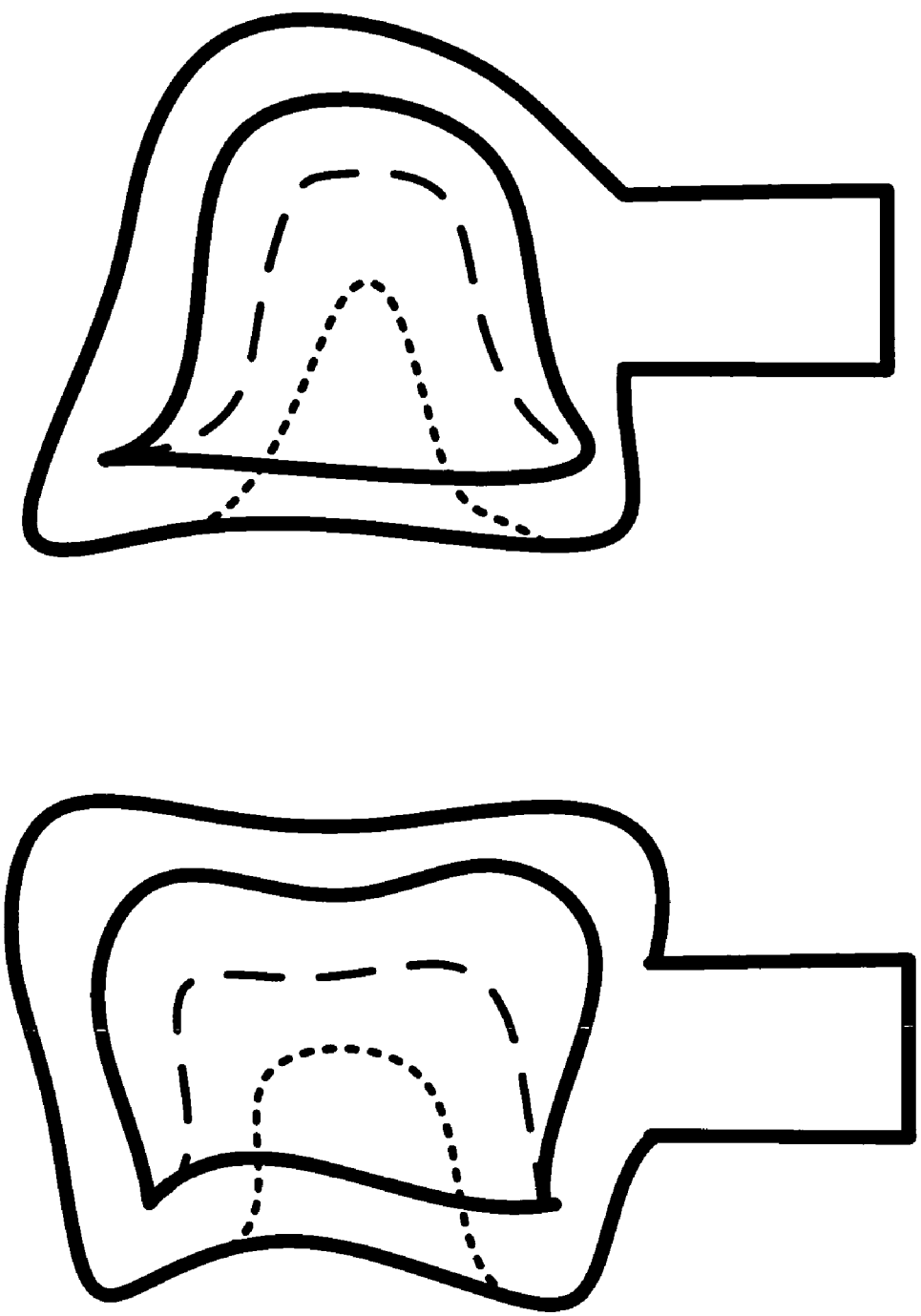
FIG. 8 illustrates a pair of smart mill blanks each having a shape and arrangement that closely approximates a final shape of a respective coping or crown.

A standard mill blank (FIG. 7) may be partially milled or machined to create the smart blank. Similarly, the milling or machining process may be simulated, e.g, by a digital processor that is suitably programmed with computer software. The milling procedure is performed on a standard mill blank and the milling or machining process terminated when the amount of material that has been removed has reached or exceeds U. This is illustrated in FIG. 8. In each case, a series of partially machined crowns or copings may be formed. A number n of test cases will result in n shapes.

A tolerance percentage factor T may be selected. A subset of the shapes determined above may be selected based on criterion such as: for each test case, there must exist in the shape library a shape where no more than TV/100 volume of material must be removed where V is the volume of the shape from the shape library. Accordingly, the larger the tolerance percentage factor T, the smaller the subset. Based on the C and T parameters and n test cases, a set of m shapes where 0<m<=n may be formed, in which the m shapes comprise a smart mill blank library. Each shape may be mass produced according to the shapes determined above.

As noted above, an integrated milling attachment (the holder or sprue) is included with each shape to provide attachment for the milling and machining process. The attachment may be formed from the same or other material as the smart mill blank.

For each smart mill blank, a partial or a full three-dimensional (3D) model or computer aided design (CAD) model for the shape and attachment may be recorded and associated with the smart blank. The 3D and CAD model information may be useful for final milling of the smart blank.

As noted above, an illustrative embodiment includes a process in which a proposed restoration is digitally scanned, using a 3D data acquisition technique. An optimum coping to fit on top of the restoration may then be determined via a computer-based matching algorithm. Every dimension (or, optionally, certain key dimensions) of the coping are determined from the digital data. This shape is compared with the library of smart mill blanks, and a smart blank selected for which conditions are satisfied. As used herein, a selection may be computer-generated, or the operator may be provided with an indication of which smart blanks "best" fit the design. In particular, the smart mill blank may be selected so that the desired coping fits entirely within the smart mill blank and so that the volume difference between the coping and smart mill blank is minimized, i.e., so that the yield is optimized.

According to another embodiment, the smart mill blank library comprises mill blanks for one or more of the following: molars, pre-molars, bicuspids, canines, upper central incisors, upper lateral incisors and lower incisors, along with some size variation allowed for different patients. In addition, the library may also use as an input variable the ethnicity and sex of the patient. Using the chosen smart mill blank as a starting point, the amount of material cut off may be minimized, thereby optimizing yield. The smart mill blank library also provides for reduced quicker machining time and reduced recovery process. The blanks may be formed from precious, semi-precious, non-precious metals, metal alloys, composite materials, or any other material suitable for dental applications. Where precious metal may be used, the invention provides much more viable alternative from an economics point of view by reducing the amount of material that is wasted and recovered.

Figure 9A:
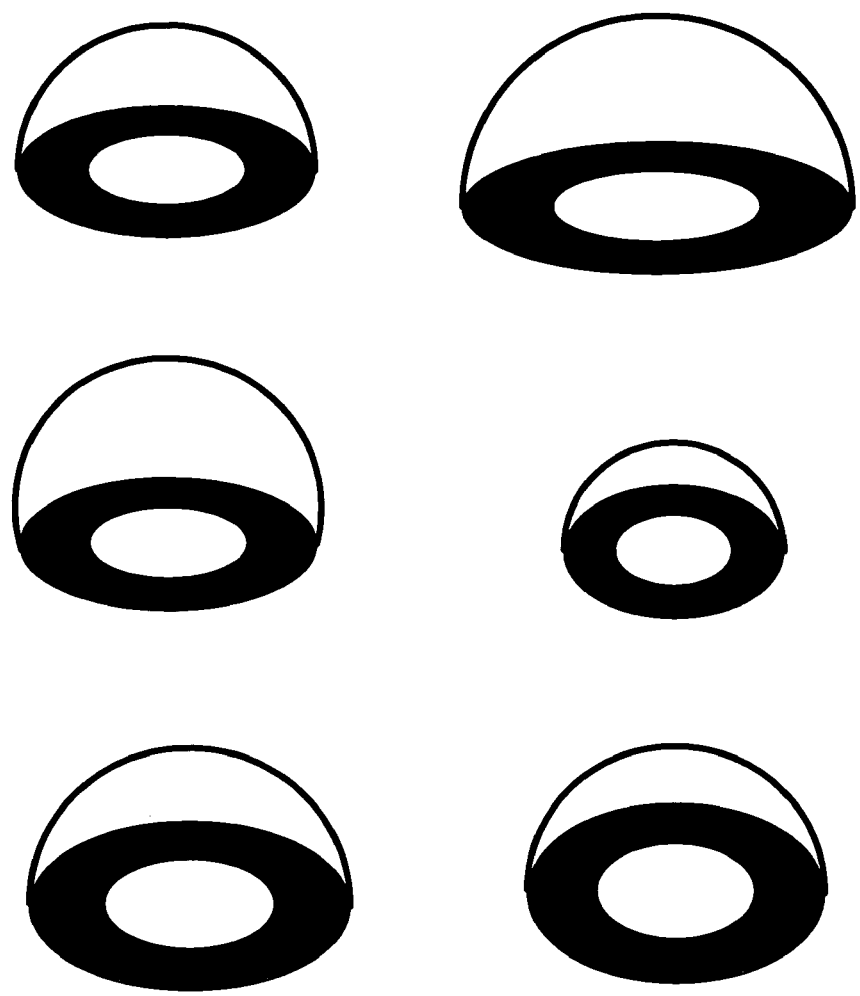
FIG. 9A illustrates a smart mill blank library of multiple mill blanks that may be selected based on size, shape and arrangement of the mill blank for the purposes of producing a coping.
Figure 9B:
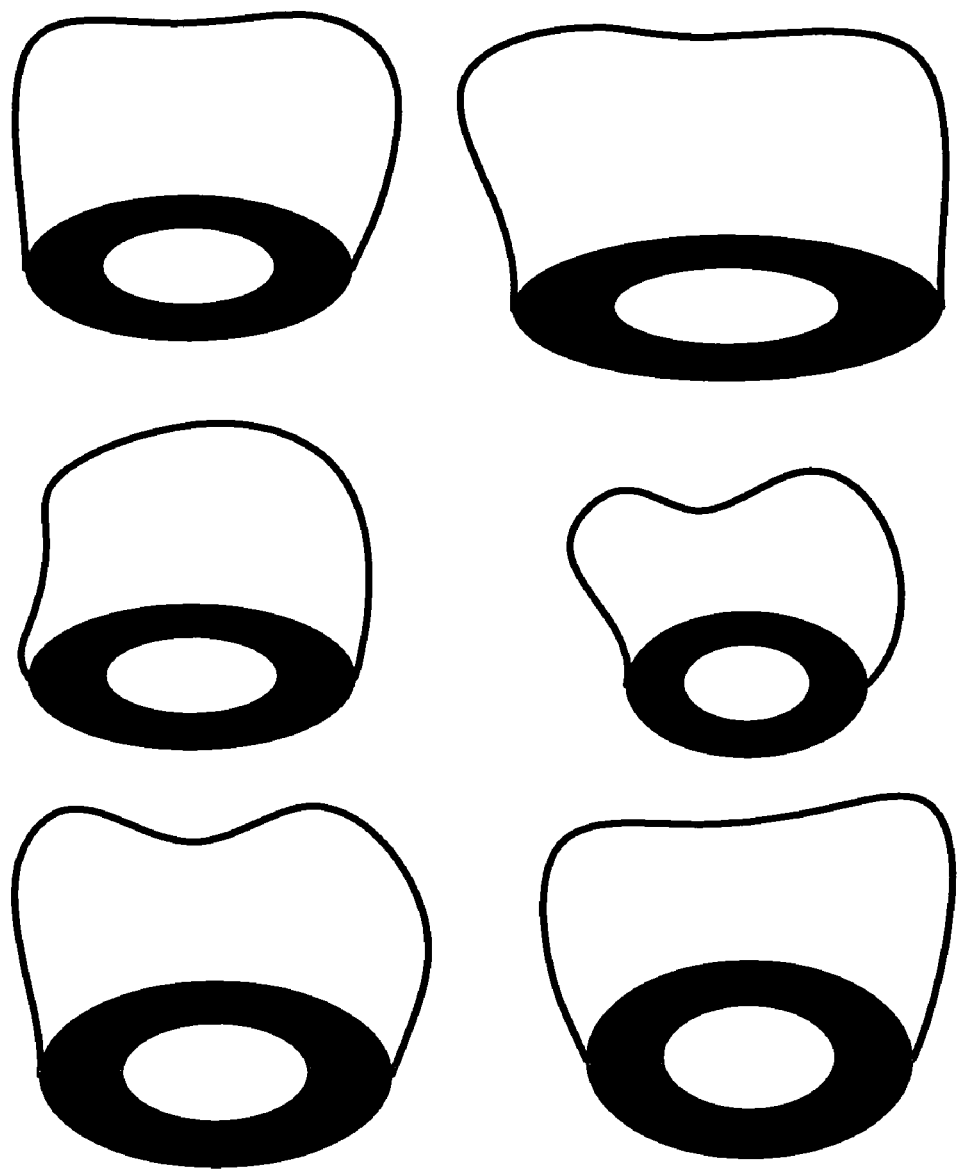
FIG. 9B illustrates a smart mill blank library of multiple mill blanks that may be selected based on size, shape and arrangement of the mill blank for the purposes of producing a full crown.

In still another embodiment, the smart mill blank library comprises a series of blanks made up of a generally convex or concavo-convex upper surface attached to a concave lower surface, with an integrated milling attachment with an orientation-specific attachment key for the milling machine. A variety of combinations may be formed with different upper surfaces attached to different lower surfaces to form a large library of smart blanks. FIG. 9B illustrates a representative library of this type.

In yet another embodiment as illustrated in FIG. 9B, the smart mill blank library comprises a set of partial spherical shells of different sizes and thicknesses. Each shell may include an integrated milling attachment. The attachment may have an orientation-specific attachment key for a milling machine. The digitally produced coping may be machined from a selected blank, for which the cut-off material is minimized during the machining process.

In a still further embodiment, the smart mill blank library comprises a series of flattened dimpled spherical solids of different sizes and thicknesses. Each solid may have an integrated milling attachment with an orientation-specific attachment key for the milling machine.

According to another embodiment, the smart mill blank library comprises a set of mill blanks appropriate for copings for one of any one of different classes of teeth, such as molars, premolars, bicuspids, canines and incisors.

In a further embodiment, the smart mill blank library comprises a set of mill blanks appropriate for crowns for one of any one of different classes of teeth, such as molars, premolars, bicuspids, canines and incisors.

Another embodiment of the invention is a smart blank library comprising a set of mill blanks appropriate for copings for many different classes of teeth, such as molars, premolars, bicuspids, canines and incisors, along with size variations in each class.

In another embodiment, the smart mill blank library comprises set of different blanks that are selected to enable all possible cases to be milled from one of the mill blanks. The general shapes of the mill blanks may be selected so that a difference in volume between the desired coping and at least one library blank is determined to be less than a predetermined tolerance. The tolerance may be determined according to economic or other reasons.

In still another embodiment, the smart mill blank library comprises two sets of blanks: a set of smart crown mill blanks to be used to mill full crowns; and a set of smart coping mill blanks to be used to mill copings. This is illustrated in FIGS. 9A and 9B. Each set is determined by examining multiple real cases and partially forming a standard mill block to make the desired coping or crown. By setting a criterion of a certain percentage of material loss that is permitted in completing the machining or milling, a subset of those partially machined or milled blanks is selected, and those shapes are used for the smart mill blank library.

While various embodiments of the invention have been described, it will be apparent to those of ordinary skill in the art that many more embodiments and implementations are possible and modifications may be made that are within the scope of the invention. It should be appreciated that the apparatuses and methods of the present invention are capable of being incorporated in the form of a variety of embodiments without departing from its spirit or essential characteristics. The described embodiments are to be considered in all respects only as illustrative and not restrictive.

As noted above, materials used to make the prostheses typically include gold, ceramics, amalgam, porcelain and composites. For dental restorative work such as fillings, amalgam is a popular choice for its long life and low cost. Amalgam also provides a dental practitioner the capability of fitting and fabricating a dental filling during a single session with a patient. The aesthetic value of amalgam, however, is quite low, as its color drastically contrasts to that of natural teeth. For large inlays and fillings, gold is often used. However, similar to amalgam, gold fillings contrast to natural teeth hues. As noted above, in the present invention, the smart blanks may be formed of any type of material normally used for dental restorations.

In the embodiments described above, each of the smart blanks in the library has a geometry that differs from the geometry of other smart blanks in the library by other than scaling. This is a preferred approach, but it is not always a requirement.

As noted above, preferably both the smart blank inventory management process and the smart blank selection process are automated, i.e., under the control of a suitably programmed processor or other controller. While certain aspects or features of the present invention have been described in the context of a computer-based method or process, this is not a limitation of the invention. Moreover, such computer-based methods may be implemented in an apparatus or system for performing the described operations, or as an adjunct to other dental milling equipment, devices or systems. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including optical disks, CD-ROMs, and magnetic-optical disks, read-only memories (ROMs), random access memories (RAMs), magnetic or optical cards, or any type of media suitable for storing electronic instructions, and each coupled to a computer system bus. The computer may be connected to any wired or wireless network. Further, the above-described functions and features may be implemented within or as an adjunct to other known dental milling equipment, devices or systems.

Further, while the above written description also describes a particular order of operations performed by certain embodiments of the invention, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic.

Having now described our invention, what we claim is as follows:

1. A method of assembling blanks for use in manufacturing dental restorations, comprising:
    given a set of blanks, selecting an assemblage of the blanks, wherein at least first and second of the blanks in the assemblage comprise a body adapted to be shaped by material removal, the body of the first blank having a geometry that differs from the body of the second blank by other than scaling, and wherein the body of each of the first and second blanks has at most one symmetric plane; and
    using that assemblage to manufacture dental restorations.

2. The method as described in claim 1 wherein the assemblage of the blanks is selected to maximize an average yield per blank, wherein the average yield per blank is calculated as a weight of a finished restoration divided by a weight of a blank prior to being shaped by material removal.

3. The method as described in claim 2 wherein the average yield per blank is a weighted average.

4. The method as described in claim 1 wherein the assemblage of the blanks is selected to balance an average yield per blank with a productivity factor.

5. The method as described in claim 1 wherein the assemblage of the blanks is selected to balance an average yield per blank with a cost factor.

6. The method as described in claim 1 wherein the assemblage of the blanks is selected to balance a set of yield, productivity, cost and tooth distribution factors.

7. An assemblage, comprising:
    a plurality of mill blanks, at least first and second of the mill blanks in the plurality each comprising a body adapted to be shaped by material removal;
    wherein the body of the first blank has a geometry that differs from the body of the second blank by other than scaling;
    wherein the body of each of the first and second blanks has at most one symmetric plane.

8. The assemblage as described in claim 7 wherein each blank includes a holder to enable the blank to be maintained within a shaping apparatus.

9. The assemblage as described in claim 7 wherein at least one of the blanks is formed of a metal or metal alloy.

10. The assemblage as described in claim 7 wherein at least one of the blanks is formed of a ceramic.

11. A method of producing dental items, comprising:
    maintaining an assemblage of "m" mill blanks, the assemblage comprising at least first and second mill blanks each comprising a body adapted to be shaped by material removal, wherein the body of the first blank has a geometry that differs from the body of the second blank by other than scaling, and wherein the body of at least one of the mill blanks in the assemblage has at most one symmetric plane;
    for a given restoration R being designed, selecting a subset $\{B_1, B_2, \ldots B_n,\}$ of "n" blanks, where $n \leq m$, such that each of the blanks of the subset contain the restoration R; and
    selecting a given one of the blanks of the subset for use in producing the restoration.

12. The method of claim 11 wherein the given one of the blanks that is selected has the smallest volume.

13. The method of claim 11 wherein the given one of the blanks that is selected has a minimal volume difference with respect to the given restoration R being designed.

14. The method of claim 11 wherein the dental item is prepared by milling the selected blank.

15. The method as described in claim 14 wherein the selected blank is milled using a computer-assisted milling machine.

* * * * *